United States Patent [19]

Slager et al.

[11] 4,259,243

[45] Mar. 31, 1981

[54] PROCESS FOR THE PREPARATION OF 2,5-DIOXO-3H, 6H-FURO(3,2-B)FURAN-3A,6A-DIACETIC ACID

[75] Inventors: James E. Slager, Union; Charles E. Brothers, Cassopolis, both of Mich.

[73] Assignee: Miles Laboratories, Inc., Elkhart, Ind.

[21] Appl. No.: 110,638

[22] Filed: Jan. 9, 1980

[51] Int. Cl.$^3$ ............................................. C07D 493/04
[52] U.S. Cl. .................................................... 260/343.6
[58] Field of Search ...................................... 260/343.6

[56] References Cited

U.S. PATENT DOCUMENTS

| | | | |
|---|---|---|---|
| 3,826,839 | 7/1974 | Sutton et al. | 260/343.6 |
| 3,895,021 | 7/1975 | Weinstock | 260/343.6 |
| 4,032,651 | 6/1977 | Aldridge et al. | 260/343.6 |
| 4,159,989 | 7/1979 | Wood | 260/343.6 |

OTHER PUBLICATIONS

F. G. and Dixon, J. Org. Chem. 24, 1959, p. 1226.

*Primary Examiner*—John D. Randolph
*Assistant Examiner*—Jane T. Fan
*Attorney, Agent, or Firm*—Jerome L. Jeffers

[57] ABSTRACT

The present invention involves a method for the preparation of the title compound which method involves reacting, in a suitable solvent, 1,4,5,8-tetrahydronaphthalene or 9,10-dihydroxy-1,4,5,8-tetrahydronaphthalene with $IO_4^-$ in the presence of a catalytic amount of $RuO_2$. The title compound is useful as a chelating agent.

9 Claims, No Drawings

PROCESS FOR THE PREPARATION OF 2,5-DIOXO-3H, 6H-FURO(3,2-b)FURAN-3a,6a-DIACETIC ACID

BACKGROUND OF THE INVENTION

A chelating agent is a compound containing donor atoms that can combine by coordinate bonding with a single metal ion to form a cyclic structure called a chelation complex or, simply, a chelate. Because the donor atoms are connected intramolecularly by chains of other atoms, a chelate ring is formed for each donor atom after the first which coordinates with the metal. Each ring gives the appearance of a metal atom being held in a pincer formed by other atoms.

The technological importance of chelation is based on the almost universal presence of metal ions of one kind or another. They are present either naturally or, in certain instances, by intentional addition. Chelating agents provide a means of manipulating and controlling metal ions by forming complexes that usually have properties that are markedly different from those of the original ions or the chelants. These properties may serve to reduce undesirable effects of metal ions as in sequestration, or to create desirable effects as in metal buffering and solubilization.

The structural essentials of a chelate are coordinate bonds between a metal ion and two or more atoms in the molecule of the chelating agent. The coordinating atoms of the chelating agent are electron donors and the metal ion is an election acceptor. When coordinate bond formation occurs between the metal and two donor atoms, the atoms of the ligand that connect the donor atoms complete the ring that gives the structure its chelate character.

Commercially useful chelating agents include ethylene-diamine tetraacetic acid (EDTA) and citric acid. Other compounds known to be useful as chelating agents include ethylenediamine-N,N'-diacetic acid, alanine-N,N'-diacetic acid, anthranil-N,N-diacetic acid and 1,2-dihydroxyanthraquinone-3-methylamine-N,N'-diacetic acid.

More recently, a novel compound; 2,5-dioxo-3H,6H-furo[3,2-b]furan-3a,6a-diacetic acid; has been found to be useful as a chelating agent having stability constants with various cations which are between EDTA and citric acid. The present invention involves a novel method for preparing this compound.

SUMMARY OF THE INVENTION

The present invention is a process for the preparation of 2,5-Dioxo-3H,6H-furo[3,2-b]furan-3a,6a-diacetic acid of the formula:

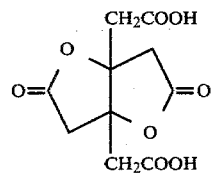

by reacting in a suitable solvent 1,4,5,8-tetrahydronaphthalene of the formula:

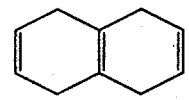

or 9,10-dihydroxy-1,4,5,8-tetrahydronaphthalene of the formula:

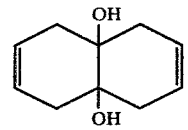

with $IO_4^-$ in the presence of a catalytic amount of $RuO_2$ for a time sufficient to form the desired product.

DETAILED DESCRIPTION AND PREFERRED EMBODIMENTS

The method of carrying out the invention is further illustrated by the following examples:

EXAMPLE I

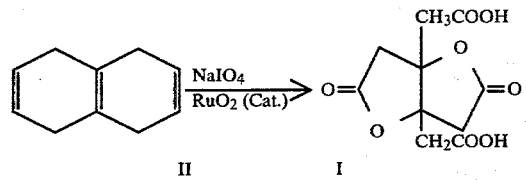

Compound II (1,4,5,8-tetrahydronaphthalene, 0.64 g, 4.8 mmol) was dissolved in 25 ml of acetone which was added to 200 ml of $H_2O$ containing 10.6 g of $NaIO_4$ and ~0.05 g of $RuO_2$. After stirring the mixture for 2 hours, 12.7 equivalents of $NaIO_4$ were utilized. The solution was then extracted with $CHCl_3$, the extracts dried with $Na_2SO_4$ (anhyd.) and the solvent stripped off the filtrate after drying. The NMR spectra of the recovered product was consistant with that of Compound I.

EXAMPLE II

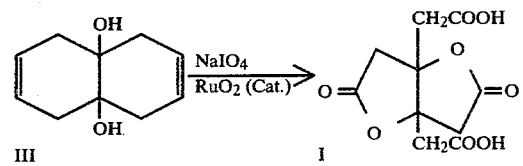

A small amount of $NaIO_4$ and, $RuO_2$ (catalytic amount) was mixed in water to produce a yellow solution. Solid III, 9,10-dihydroxy-1,4,5,8-tetrahydronaphthalene, was added proportionwise such that the last portion deposited a permanent black precipitate indicating that all the $NaIO_4$ had been utilized. Thus, the isnoluble $RuO_2$ deposited in place of the soluble $RuO_4$ (yellow solution). Thin, layer chromatography (TLC) of the reaction mixture was negative for ketone indicating that I is the product based on the results of Example I and the following analysis:

It is known that periodate can oxidize certain vicinal-glycols but III was found to be very resistant to such oxidation under ambient conditions as determined by titration of the reaction solution for $IO_4^-$ prior to the addition of $RuO_2$ which indicated no measurable change in the concentration of $IO_4^-$ over a period of about two hours. However, a reaction was observed when a catalytic amount of $RuO_2$ ($RuO_2 + IO_4^- \rightarrow RuO_4$) was added. Further, the literature* suggests the use of $RuO_4$ to catalyze the oxidation of olefins to vicinal glycols. The resulting vicinal-glycol would, unlike the 9,10-dihydroxy moiety in III, be quite unhindered for further $IO_4^-$ oxidation, for example:

*Oberender, F.G. and Dixon, J.A. *J. Org. Chem.* 24, (1959) p. 1226.
Sarel, S. and Yanuku, Y., *J. Org. Chem.*, 24. (1959) p. 2018.

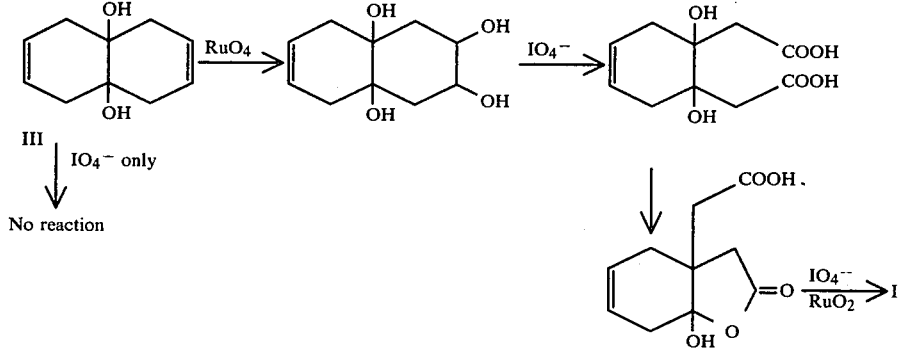

The absence of a ketone group observable by TLC negates this alternate reaction mechanism:

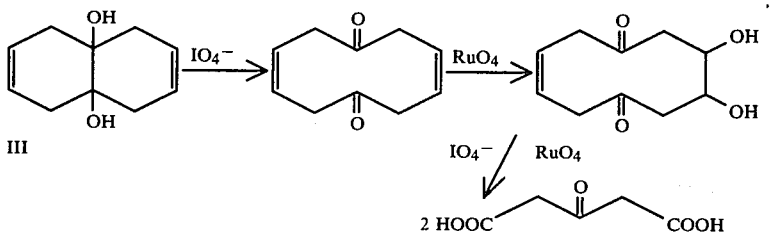

EXAMPLE III

To a stirred 2 liter beaker containing about 1100 ml of $NaIO_4$-$HIO_4$ mixture in aqueous solution (0.91 moles $IO_4^-$), sufficient concentrated $H_2SO_4$ to result in pH 0.5–0.9 and 0.05 g (0.4 mmole) $RuO_2$ and 10 g (0.076 mole) of II (1,4,5,8-tetrahydronaphthalene) is added in portions while maintaining the temperature at a range of from 20° to 55° C. The desired product, I, precipitated from the reaction solution upon cooling and was filtered off, washed with cold water and recrystallized.

Reactants II or III can be added to the reaction mixture either as solids or as a solution in such solvents as chloroform, carbon tetrachloride, acetone, acetic acid or dioxane-water mixtures, generally over a period of about 30 minutes. The progress of the reaction can be followed by determination of the $IO_4^-$ remaining in the sample of the reaction solution versus time and when 0.76 or more moles (10 equivalents) of $IO_4^-$ had disappeared, the reaction described in Example III was considered finished; at the 55° temperature about 2 hours was sufficient. Lower temperatures require longer reaction times. The product can be recrystallized from hot water or hot alcohol-water solution. Typically, yields of up to 45% (based on II or III) can be achieved.

Any source of the $IO_4^-$ ion in solution will effect the transformation described in Examples I–III, the only further requirement being the maintenance of a solution such that the product can be isolated by filtration without co-precipitation of some other by-product (e.g. $NaIO_3$ is insoluble if the pH is too high). In practicle terms this would constrain one to $HIO_4$, $NaIO_4$, $KIO_4$ and the other Group IA elements of the periodic Table as cations unless one otherwise solubilizes the $IO_4^-$ and resulting $IO_3^-$ ions. Alternatively, isolation of the product by different means (e.g. complexation, extraction, etc.) could bypass even the solubility problem.

EXAMPLE IV

Stability Constants of Metals with 2,5-Dioxo-3H,6H furo[3,2-b]furan 3a,6a-diacetic acid (lactone).

The procedure for determining stability constants for (lactone) with various metals by the method of R.W. Schmid and C.N. Reilly, JACS 78, 5513 (1956) was used.

The cell consisted of a 50 ml beaker, a glass electrode, a J-tube mercury electrode and a saturated calomel electrode. About 30 ml of the solution was taken for measurement and stirred by means of a magnetic stirrer. The pH was varied by dropwise addition of sodium hydroxide or perchloric acid. The pH was measured with a Corning Model 125 pH meter and the potential by the same Corning Model 125 meter. Equilibrium within ±1 mμ generally was reached in one minute.

100 ml solutions were made up to contain 0.1 molar $NaClO_4$, 0.0001 moles $HgCl_2$, 0.0007 molar lactone and 0.001 moles of the metal to be tested.

TABLE I

| Experimental data: Metal | Constant voltage with varying pH |
|---|---|
| Cu++ | .247 volts |
| Mg++ | .308 |
| Fe++ | .245 |
| Cd++ | .260 |
| Zn++ | .255 |
| CO++ | .264 |
| Mn++ | — |
| Ni++ | — |
| Pb++ | — |

The stability constant Log $K_{MeLac}$ can be calculated from the equation ①

① $E$ measured =

$$E^\circ_{Hg} + 0.0296 \log \frac{[C_{me}][C_{HgLac}]}{[C_{MeLac}] K_{HgLac}} + 0.0296 \log K_{MeLac}$$

In this equation $K_{HgLac}$ is unknown, however a close approximation can be determined by comparing the potential of Hg EDtA solution and Hg Lac solution at the same concentration & pH. At pH 4 the following data was obtained E measured Hg EDtA 0.200
E measured Hg Lac 0.318
K Hg EDtA from Lit. 22.1
Therefore $$K_{HgLac} = 22.1$$

$$\frac{.6105 - .318}{.0296} \quad \frac{.6105 - .200}{.0296}$$

$$K_{HgLac} = 15.7$$

Using this value in equation 1 it reduces to the following $E$ measured =

$$0.6105 + 0.0296 \log \frac{4 \times 10 - 4 \times 1 \times 10 - 4}{6 \times 10 - 6}$$

$$0.0296 \times 15.7 + 0.0296 \log K_{MeLac}$$

$$\text{Log } K_{MeLac} = \frac{-0.6105 - E \text{ measured}}{0.0296} + 4.18 - 15.7$$

$$\text{Log } K_{MeLac} = 19.88 - \frac{0.6105 - E \text{ measured}}{0.0296}$$

Using the data from Table 1 the following values are obtained

TABLE II

| Metal | Lactone | EDtA[1] | Citric acid[2] |
|---|---|---|---|
| Hg++ | 15.7 | 22.1 | 11.1 |
| Cd++ | 8.0 | 16.4 | 3.1 |
| Mg++ | 9.6 | 8.9 | — |
| Cs++ | 7.6 | 10.7 | 3.9 |
| Fe++ | 7.6 | — | 3.0 |
| Cu++ | 7.6 | 18.7 | 7.3 |
| Zn++ | 7.9 | 16.4 | 5.5 |
| Pb++ | — | 17.9 | 5.7 |
| Mn++ | — | 13.8 | 5.6 |
| Co++ | 7.8 | — | — |

TABLE II-continued

| Metal | Lactone | EDtA[1] | Citric acid[2] |
|---|---|---|---|
| Ni++ | — | — | — |

[1] From Schmid and Reilly JACS 78, 5573 (1956)
[2] By above method

From Table II it can be determined that the stability constants of various metal ions with the compound of the present invention are intermediate between those of EDTA and citric acid indicating utility as a chelating agent.

What is claimed is:

1. A method for the preparation of 2,5-Dioxo-3H,6H-furo[3,2-b]furan-3a,6a-diacetic acid of the formula:

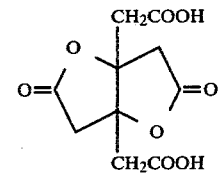

by reacting, in a suitable solvent 1,4,5,8-tetrahydronapthalene of the formula:

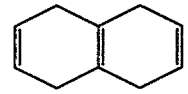

or 9,10-dihydroxy-1,4,5,8-tetrahydronapthalene of the formula:

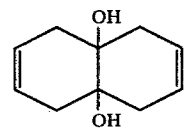

with $IO_4^-$ in the presence of a catalytic amount of $RuO_2$ for a time sufficient to form the desired product.

2. The method of claim 1 wherein the temperature is maintained at a range of from 20° to 55° C.

3. The method of claim 1 wherein the solvent is water.

4. The method of claim 1 wherein the source of $IO_4^-$ is $HIO_4$.

5. The method of claim 1 wherein the source of $IO_4^-$ is $MIO_4$ where M represents a group IA cation.

6. The method of claim 5 wherein M is potassium.

7. The method of claim 5 wherein M is sodium.

8. The method of claim 1 wherein the organic reactant is 1,4,5,8-tetrahydronapthalene.

9. The method of claim 1 wherein the organic reactant is 9,10-dihydroxy-1,4,5,8-tetrahydronapthalene.

* * * * *